United States Patent
Frank et al.

(10) Patent No.: US 7,702,376 B2
(45) Date of Patent: Apr. 20, 2010

(54) METHOD FOR ECG-TRIGGERING A MEASURING SEQUENCE OF A MAGNETIC RESONANCE DEVICE

(75) Inventors: Michael Frank, Erlangen (DE); Stefan Merkel, Erlangen (DE); Ernst Mustafa, Fürth (DE); Helmut Wrobel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 226 days.

(21) Appl. No.: 11/440,818

(22) Filed: May 25, 2006

(65) Prior Publication Data

US 2007/0167737 A1  Jul. 19, 2007

(30) Foreign Application Priority Data

Jun. 14, 2005 (DE) ............ 10 2005 027 438

(51) Int. Cl.
*A61B 5/055* (2006.01)

(52) U.S. Cl. .................. 600/413; 600/428

(58) Field of Classification Search ............ 600/413, 600/428
See application file for complete search history.

(56) References Cited

U.S. PATENT DOCUMENTS

| | | | | |
|---|---|---|---|---|
| 3,654,916 A | * | 4/1972 | Neilson | 600/515 |
| 5,087,348 A | * | 2/1992 | Dai et al. | 208/111.15 |
| 5,987,348 A | * | 11/1999 | Fischer et al. | 600/413 |
| 6,070,097 A | * | 5/2000 | Kreger et al. | 600/521 |
| 6,144,201 A | * | 11/2000 | Miyazaki | 324/306 |
| 6,501,979 B1 | * | 12/2002 | Manning et al. | 600/413 |
| 6,675,036 B2 | * | 1/2004 | Kreger et al. | 600/413 |
| 6,708,052 B1 | * | 3/2004 | Mao et al. | 600/407 |
| 6,801,800 B2 | * | 10/2004 | Miyazaki et al. | 600/410 |
| 6,889,071 B2 | * | 5/2005 | Saranathan et al. | 600/413 |
| 6,892,092 B2 | * | 5/2005 | Palreddy et al. | 600/509 |
| 6,937,883 B2 | * | 8/2005 | Prince | 600/411 |
| 7,047,060 B1 | * | 5/2006 | Wu | 600/413 |
| 7,286,871 B2 | * | 10/2007 | Cohen | 600/544 |
| 2003/0225328 A1 | * | 12/2003 | DeMeester et al. | 600/419 |
| 2004/0073124 A1 | * | 4/2004 | Axel | 600/509 |

FOREIGN PATENT DOCUMENTS

WO  WO 99/04688 A1  2/1990
WO  2004008960 A1  1/2004

* cited by examiner

*Primary Examiner*—Brian Casler
*Assistant Examiner*—Peter Luong

(57) ABSTRACT

Method for ECG triggering a measuring sequence of a magnetic resonance device, with ECG signals of a patient being detected over two channels, with the triggering of the measuring sequence being carried out when the ECG signal of at least one channel, said ECG signal being subjected to a digital signal processing, exceeds a threshold value, and at the same time the derivation of the ECG signal or the norm of the derivation of the ECG signal lies within a defined interval in both channels.

11 Claims, 2 Drawing Sheets

METHOD FOR ECG-TRIGGERING A MEASURING SEQUENCE OF A MAGNETIC RESONANCE DEVICE

CROSS REFERENCE TO RELATED APPLICATIONS

This application claims priority of German application No. 10 2005 027 438.2 filed Jun. 14, 2005, which is incorporated by reference herein in its entirety.

FIELD OF THE INVENTION

The invention relates to a method for ECG-triggering a measuring sequence of a magnetic resonance device, in which ECG signals of a patient are detected over two channels.

BACKGROUND OF THE INVENTION

It is necessary for magnetic resonance tomography (MR) to detect the ECG signals of the patients in order to synchronize the triggering of the MR measuring sequences to the heart beat of the patient. Likewise, the ECG signal detected during an MR examination allows the information about the current heart phase to be acquired. If the ECG signals and the triggering of the measuring sequence are not synchronized, there is a danger that the MR images contain movement artifacts.

In practice however there are difficulties associated with the detection of the ECG signals, since the electrical and magnetic fields acting during the MR sequences significantly interfere in the ECG electronics circuit, whereby the reliable determination of the heart phase is impaired. Aside from these undesired interferences in the ECG electronics circuit, the so-called magnetohydrodynamic effect occurs in the case of a higher magnetic fluid densities, which results in a superelevation of the T wave of the heart beat. The different phases of the heart cycle are indicated in the electrocardiography using letters, for instance by the sequence P-Q-R-S-T. Here the R wave shows the greatest deflection. It is the center of reference of the triggering and must therefore be reliably determined.

A method for ECG triggering a measuring sequence in a magnetic resonance device is known from U.S. Pat. No. 6,070,097. However, the ECG signals of a patient are detected there via a single channel.

The detection of two ECG channels has been proposed in WO 99/04688, a vector display in a coordinate system being derived therefrom. The R wave of the heart cycle should be able to be taken from this display. It is however doubtful whether this method is satisfactorily reliable as this vector projection is dependent on many influences, for instance it changes if the patient holds his/her breath.

SUMMARY OF THE INVENTION

The problem underlying the invention is thus to specify a method for triggering a measuring sequence in a magnetic resonance device, which functions reliably and trouble-free.

To solve this problem, provision is made in accordance with the invention with a method of the type mentioned at the outset that the triggering of the measuring sequence occurs when the ECG signal of at least one channel, said ECG signal being subjected to a digital signal processing, exceeds a threshold value, and at the same time the derivation of the ECG signal or the norm of the derivation of the ECG signal with two channels lies within a defined interval.

With the method according to the invention, a triggering, in other words a release of the measuring sequence of the magnetic resonance device, only takes place when a number of conditions are fulfilled at the same time. In accordance with the invention, the two channels for the ECG signals are evaluated separately. A triggering only takes place when a defined threshold value is exceeded in at least one channel. The derivation of the ECG signal or its norm must lie within a defined interval or value range and is used as a further criterion. The triggering of the measuring sequence is only carried out when this condition is fulfilled for both channels.

In accordance with the invention, the criteria determination is carried out in parallel so as to minimize delay times. In accordance with the invention, the parallel extraction of the criteria determination can be almost arbitrarily expanded by further criteria. In this case, the triggering is the result of a special criteria weighting.

There can be provision in accordance with the invention for the digital signal processing of the ECG signals to comprise the following steps: a low-pass filtering which is adapted to the MR-specific disturbances, and/or calculation of a derivation norm function and/or calculating the threshold value by means of an interpolator. In this case, the derivation norm function can be formed on the basis of the first or second derivation of the ECG signal or a combination thereof.

With the method according to the invention, a lower and an upper limit value can be determined in each instance for both channels, said limit values defining the interval. An especially highly reliable method is produced if the limit values defining the interval are determined in a learning phase, whilst none or at the most negligible disturbances occur during the detection of the ECG signals. It is particularly beneficial if the patient is positioned outside a patient tunnel of the magnetic resonance device during the learning phase, as the signal detection is not influenced in this case by the magnets of the magnetic resonance device. An even higher reliability can be achieved if a further learning phase is carried out prior to another magnetic resonance examination. This can also be carried out in the patient tunnel. This enables changes occurring in the meantime, which can be caused for instance by the administration of a drug, to be compensated for.

The invention further relates to a magnetic resonance device. The magnetic resonance device according to the invention is designed to implement the described method.

BRIEF DESCRIPTION OF THE DRAWINGS

Further advantages and details of the invention are explained on the basis of an exemplary embodiment with reference to the figures. The figures are schematic representations in which.

DETAILED DESCRIPTION OF THE INVENTION

Figure 1:
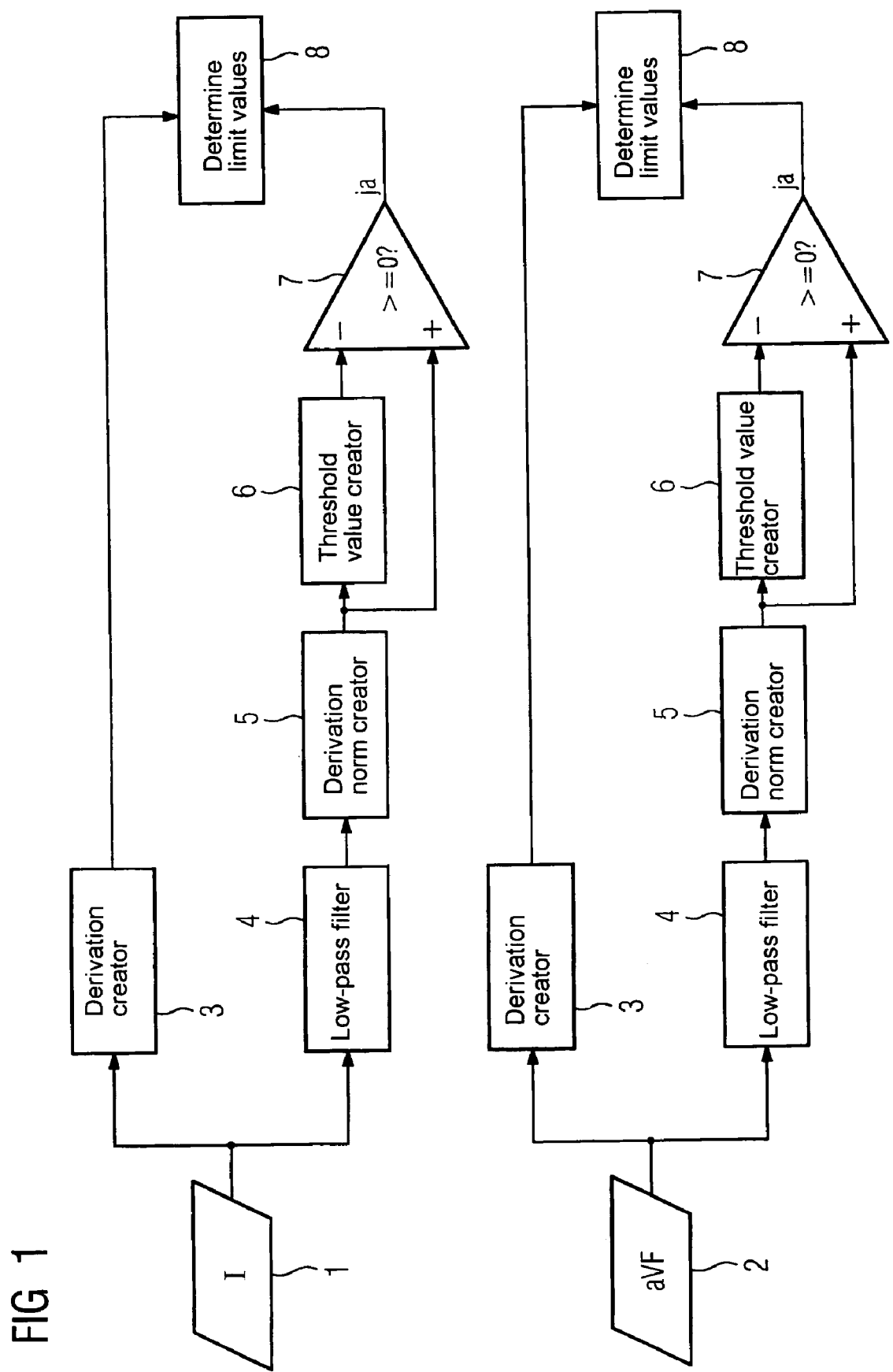
FIG. 1 shows a schematic representation of the learning phase of the method according to the invention.

A shown in FIG. 1, digital input data is received via ECG channels 1 and 2. The channel 1 corresponds here to the derivation I, and the channel 2 corresponds to the derivation aVF. The initial learning phase shown in FIG. 1 is carried out before the actual magnetic resonance measurement; the patient is thus positioned outside the patient tunnel. This ensures that the signal detection is not interrupted by magnetic or electrical fields in the inside of the patient tunnel. The limit values for the R wave of the ECG signals are defined in the learning phase. The lower and the upper limit value thus define an interval which determines the reliable value range for the R wave.

As shown in FIG. 1, the signals are fed to a derivation creator 3, which forms the derivation or the norm of the derivation. A low pass filter 4 is passed through in the lower branch, said low pass filter 4 being tailored to the interferences occurring in the magnetic resonance device. The derivation norm function is finally formed in a derivation norm creator 5. In this way, the first or the second derivation of the signals or a combination thereof can be used. A threshold value is determined in a threshold value creator 6 by means of an interpolator, said threshold value being compared in a comparator 7 with the output value of the derivation norm creator 5. The maximum and minimum of the derivation is determined in this way and stored in step 8. The maximum and the minimum are the limit values for the interval of the reliable values. The maximum of the derivations value and/or of the derivation norm value delimits the R wave compared with the steep edged gradient interferences. Fault triggerings on the lesser steep edged T waves of the heart cycle are obviated by the lower limit value. Further algorithmic modules can be integrated within the method, from which algorithmic modules further trigger criteria or boundary criteria result.

The limit values of the interval determined in the initial learning phase are taken into account during the MR examination carried out in connection therewith. The limit values or a subset thereof are optionally adjusted or updated during further learning phases in the patient tunnel.

The digital signal processing for the second channel 2 is carried out in a similar way to the first channel. The signal is likewise processed in two separate branches, so as to achieve the upper and the limit value for the second channel.

Figure 2:
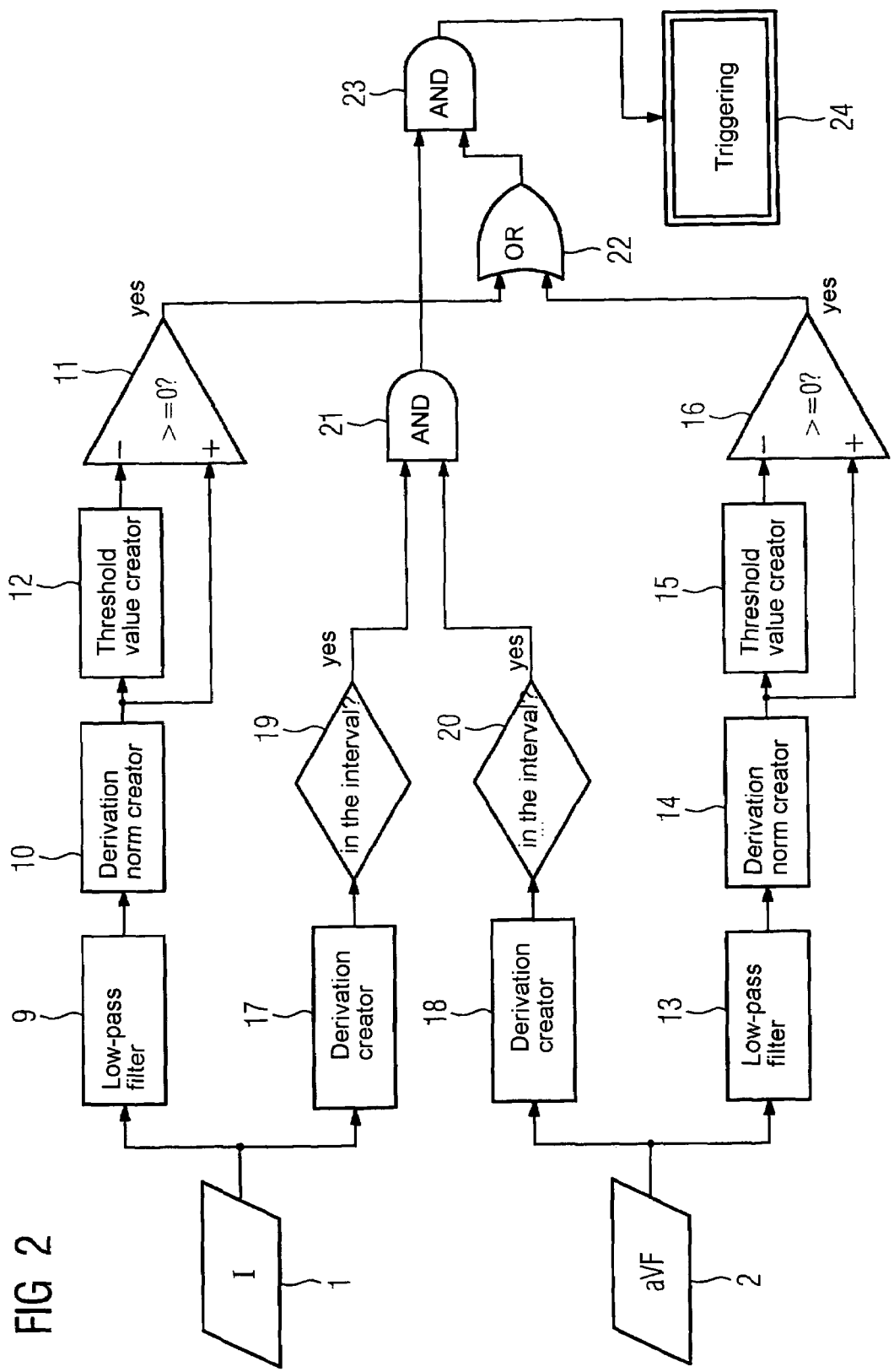
FIG. 2 shows a schematic representation of the method according to the invention.

FIG. 2 shows a schematic representation of the trigger algorithm in the active phase.

The input data of the first channel 1 reaches a low pass filter 9 in the upper branch and subsequently arrives at a derivation norm creator 10. The value determined by the derivation norm creator 10 is compared in a comparator 11 with a threshold value supplied by a threshold value creator 12. The course of this digital signal processing corresponds in each instance to the lower branch of the learning phase shown in FIG. 1.

This same signal processing with a low pass filter 13, a derivation norm creator 14, a threshold value creator 15 and a comparator 16 is carried out for the lower branch of the second channel 2.

In the respective other branch of the first and of the second channel 1, 2, a derivation creator 17 and/or 18 is used, which supplies the derivation or the norm of the derivation of the respective ECG signal. Finally, an examination is carried out for both channels separately in the method step 19 and 20 as to whether the value supplied by the derivation creator 17, 18 lies within the defined interval. So that this condition is fulfilled, the value must lie between the lower and the upper limit value, which were determined in the preceding learning phase. Both branches are linked to one another by an AND function 21, in other words the method is continued only when the derivations of both channels 1, 2 lie within their respective reliable value ranges.

FIG. 2 shows that the upper branch of the first channel and of the lower branch of the second channel are linked to one another by an OR function 22, in other words the trigger algorithm is continued when the threshold value of the first channel or the threshold value of the second channel or both threshold values are exceeded. The output signal of the AND link 21 and the output signal or the OR link 22 are supplied to an AND link 23. A triggering 24 is only carried out when the two conditions are fulfilled.

The invention claimed is:

1. A method for electrocardiogram (ECG) triggering of a measuring sequence of a magnetic resonance device, comprising:
   detecting a first ECG signal and a second ECG signal of a patient via a first ECG channel and a second ECG channel;
   generating a respective derivation or a respective norm of the derivation of the first and second ECG signals;
   signal processing the first and second ECG signals to create respective threshold values of the first and second ECG signals;
   determining when any one of the first and second ECG signals exceeds a corresponding threshold value;
   determining, in both the first ECG channel and the second ECG channel, when the respective derivation or the respective norm of the derivation of both the first and second ECG signals are simultaneously within respective intervals of the first and second ECG channels, wherein one of the intervals of the channels is defined based on a lower and upper limit values of a respective one of the first and second ECG signals; and
   triggering the measuring sequence upon a concurrent determination that 1) any one of the first and second ECG signals exceeds the corresponding threshold value, and 2) that, in both the first ECG channel and the second ECG channel, the respective derivation or the respective norm of the derivation of both the first and second ECG signals are simultaneously within the respective intervals of the first and second ECG channels.

2. The method as claimed in claim 1, further comprising performing the triggering when a R wave of the one ECG signal appears on an ECG detector.

3. The method as claimed in claim 1, further comprising releasing the measuring sequence of the magnetic resonance device concurrent with the triggering of the measuring sequence of the magnetic resonance device.

4. The method as claimed in claim 1, wherein the signal processing of a respective one of the first and second ECG signals is digital and comprises:
   low pass filtering an interference of the magnetic resonance device from the one ECG signal;
   calculating a derivation norm function of the one ECG signal; and
   calculating a threshold value of the one ECG signal by an interpolator.

5. The method as claimed in claim 4, wherein the calculating of the derivation norm function of the one ECG signal is based on a first or second derivation of the one ECG signal or a combination thereof.

6. The method as claimed in claim 1, further comprising determining the lower and upper limit values of the one interval in a learning phase.

7. The method as claimed in claim 6, wherein the determining of the lower and upper limit values of the one interval occurs in an initial learning phase which is prior to a magnetic resonance measurement with a patient positioned outside a patient tunnel of a magnetic resonance device.

8. The method as claimed in claim 6, further comprising redefining the lower and upper limit values of the one interval prior to a magnetic resonance measurement or prior to a further magnetic resonance measurement with a patient positioned inside a patient tunnel of a magnetic resonance device.

9. A magnetic resonance device with electrocardiogram (EGG) triggering of a measuring sequence of the magnetic resonance device, comprising:

a first ECG detector and a second ECG detector for detecting a first ECG signal and a second ECG signal of a patient via a first ECG channel and a second ECG channel;

a first derivation creator and second derivation creator for generating a respective derivation or a respective norm of the derivation of the first ECG signal and the second ECG signal;

respective first and second low-pass filters for filtering an interference occurring in the magnetic resonance device from the first and second ECG signals;

a first derivation norm creator and a second derivation norm creator for calculating respective derivation norm functions of the first and second ECG signals; and respective first and second interpolators for calculating respective threshold values of the first and second ECG signals;

a processor including a first module configured to determine when any one of the first and second ECG signals exceeds a corresponding threshold value, said processor further including a second module configured to determine when, in both the first ECG channel and the second ECG channel, the respective derivation or the respective norm of the derivation of both the first and second ECG signals are simultaneously within a respective interval of ECG signal values in the first and second ECG channels, wherein said processor is configured to trigger the measuring sequence upon a concurrent determination by the first and second modules that 1) any one of the first and second ECG signals exceeds the corresponding threshold value, and 2) that, for both the first ECG channel and the second ECG channel, the respective derivation or the respective norm of the derivation of both the first and second ECG signals are simultaneously within the respective intervals of the first and second ECG channels.

10. A magnetic resonance device with electrocardiogram (ECG) triggering of a measuring sequence of the magnetic resonance device, comprising:

a first ECG detector and a second ECG detector for detecting a first ECG signal and a second ECG signal of a patient via a first ECG channel and a second ECG channel;

a first derivation creator and second derivation creator for generating a respective derivation or a respective norm of the derivation of the first ECG signal and the second ECG signal;

respective first and second low-pass filters for filtering an interference occurring in the magnetic resonance device from the first and second ECG signals;

a first derivation norm creator and a second derivation norm creator for calculating respective derivation norm functions of the first and second ECG signals; and respective first and second interpolators for calculating respective threshold values of the first and second ECG signals;

a processor including a first module configured to determine when any one of the first and second ECG signals exceeds a corresponding threshold value, said processor further including a second module configured to determine when, in both the first ECG channel and the second ECG channel, the respective derivation or the respective norm of the derivation of both the first and second ECG signals are simultaneously within a respective interval of the first and second ECG channels, wherein one of the intervals of the channels is defined based on a lower and upper limit values of a respective one of the first and second ECG signals, wherein said processor is configured to trigger the measuring sequence upon a concurrent determination by the first and second modules that 1) any one of the first and second ECG signals exceeds the corresponding threshold value, and 2) that, for both the first ECG channel and the second ECG channel, the respective derivation or the respective norm of the derivation of both the first and second ECG signals are simultaneously within the respective intervals of the first and second ECG channels.

11. The magnetic resonance device as claimed in claim 10, further comprising a storage device, wherein the lower and upper limit values of the one interval are determined and stored in said storage device.

* * * * *